United States Patent
Feldman et al.

[11] Patent Number: 6,112,115
[45] Date of Patent: Aug. 29, 2000

[54] METHOD AND APPARATUS FOR DETERMINING CARDIAC PERFORMANCE IN A PATIENT

[76] Inventors: Marc D. Feldman, 16650 Huebner Rd., Apt. 1728, San Antonio, Tex. 78248; Clarence Wu, 1137 Shady Ave., Pittsburgh, Pa. 15232; Christine Mahler, 1841 Dolphin Dr., Allison Park, Pa. 15101

[21] Appl. No.: 09/265,092

[22] Filed: Mar. 9, 1999

[51] Int. Cl.[7] .................................................. A61B 5/029
[52] U.S. Cl. .......................................................... 600/513
[58] Field of Search ................................... 600/513, 526, 600/483, 484, 485

[56] References Cited

U.S. PATENT DOCUMENTS

| | | |
|---|---|---|
| 4,854,327 | 8/1989 | Kunig . |
| 5,370,122 | 12/1994 | Kunig et al. . |
| 5,450,850 | 9/1995 | Iinuma . |

*Primary Examiner*—Scott M. Getzow
*Attorney, Agent, or Firm*—Ansel M. Schwartz

[57] ABSTRACT

The present invention pertains to an apparatus for determining cardiac performance in a patient. The apparatus comprises a conductance catheter which can be excited with multiple frequencies for measuring instantaneous volume of a heart chamber. The apparatus comprises a mechanism for measuring instantaneous pressure of the heart chamber. The apparatus comprises a mechanism for processing the instantaneous volume and the pressure of the heart chamber to identify mechanical strength of the chamber and for automatically producing a plurality of desired waveforms at desired frequencies for the conductance catheter. The processing mechanism is connected to the pressure measuring mechanism and the volume measuring mechanism. The present invention pertains to a method for determining cardiac performance in a patient. The method comprises the steps of applying automatically multifrequencies to a conductance catheter. Then there is the step of measuring the instantaneous volume of a heart chamber of the patient. Next there is the step of measuring the instantaneous pressure of the heart chamber. Then there is the step of identifying mechanical strength of the chamber from the instantaneous volume and pressure.

16 Claims, 2 Drawing Sheets

METHOD AND APPARATUS FOR DETERMINING CARDIAC PERFORMANCE IN A PATIENT

FIELD OF THE INVENTION

The present invention is related to determining cardiac performance in a patient. More specifically, the present invention is related to determining cardiac performance in a patient with a conductance catheter which can be excited with multiple frequencies.

BACKGROUND OF THE INVENTION

Although there are other methods to measure ventricular volumes such as MRI and nuclear technologies, they cannot do so instantaneously. Echocardiography can generate an estimate of instantaneous volume using the modified Simpsons rule or "stack of discs". Because it utilizes a single tomographic plane to estimate three dimensional volumes, it has limitations when applied to patients with regional wall motion abnormalities. Therefore, only improvements in conductance technology offer the ability to make these precise mechanical measurements.

One conductance apparatus commercially available is the Cardiac Function Analyzer made by CardioDynamics in the Netherlands. This apparatus includes the Leycom Sigma 5, a device which is used to measure instantaneous volume from a conductance catheter. The Leycom Sigma 5 has been able to generate adequate volume data in ventricular chambers of large animals which are smaller than 150 ml. However, in patients with congestive heart failure, hearts may range from 180 to 500 ml. It has been previously shown (Reprint 1) that the Sigma 5 cannot generate a homogeneous electric field for volumes seen in human heart failure. Furthermore, there is no built in mechanism for the Sigma 5 to correct for current leakage into the surrounding conductive structures such as myocardium. As a result, it significantly underestimates the stroke volume (volume of blood pumped by the failing heart) and overestimates end-systolic and end-diastolic volumes. In reprints 2–5, there was an average 2-fold underestimation of the stroke volume. U.S. Patent to Carlson teaches that parallel conductance (current leakage outside the blood volume i.e., heart muscle) will be constant at different frequencies, so that this term can be excluded (see column 4, item (6)). Gwane et al. J Appl Physiology vol 63, pg 872–876, 1987 teaches that parallel conductance does vary with frequency, while stroke volume is constant. The present invention is based on the discovery that since muscle resistivity does vary with frequency and blood does not, the resistivity ratio of blood and muscle will vary with frequency. Hence, both the field density within the left ventricle and the current leakage to the surrounding heart muscle both vary with frequency. The end result is both stroke volume and parallel conductance varying with frequency, which is in contrast to both the Carlson patent and Gwane paper. The apparatus uses a digitally controlled signal synthesizer to drive any conductance catheter. This results in more consistent control over waveform shape, amplitude, and frequency than known before. The use of the digital synthesizer also allows the user to select any type of waveform over a broad range of frequencies to apply to a conductance catheter. The digital signal synthesizer is a Signametrics Complex DDS Generator. The device can couple with commercially available conductance catheters made by numerous vendors. One includes Millar Instruments in Houston, Tex. They market conductance catheters with an incorporated Mikrotip pressure transducer for small animals including transgenic mice (SPR 719) and humans (SPC 550, 560, and 570).

The ability to delete single genes from small animals (mice and rats) to generate transgenic animals is now possible. This allows the study of the effect of a single gene deletion on the development on congestive heart failure (weak heart muscle) and hypertrophy (thickened heart muscle). Investigators are currently utilizing left ventricular pressure or its first derivative (dP/dt); or dimension and fractional shortening (derived by echocardiography). The problem with these isolated pressure and dimension measurements is that they are altered just by the heart size changes which accompany congestive heart failure and hypertrophy. Conductance catheter pressure-volume measurements miniaturized for the transgenic mouse allows the physiologic endpoint of how weak the heart muscle has become to be accurately determined. See "Cardiac physiology in transgenic mice" by James et al., and another paper demonstrating the technique of conductance PV loops in the mouse (Georgakopoulos et al. Am J Physiology 1998), both of which are incorporated by reference herein.

SUMMARY OF THE INVENTION

The present invention pertains to an apparatus for determining cardiac performance in a patient. The apparatus comprises a conductance catheter which can be excited with multiple frequencies for measuring instantaneous volume of a heart chamber. The apparatus comprises a mechanism for measuring instantaneous pressure of the heart chamber. The apparatus comprises a mechanism for processing the instantaneous volume and the pressure of the heart chamber to identify mechanical strength of the chamber and for automatically producing a plurality of desired waveforms at desired frequencies for the conductance catheter. The processing mechanism is connected to the pressure measuring mechanism and the volume measuring mechanism.

The present invention pertains to a method for determining cardiac performance in a patient. The method comprises the steps of applying automatically multifrequencies to a conductance catheter. Then there is the step of measuring the instantaneous volume of a heart chamber of the patient. Next there is the step of measuring the instantaneous pressure of the heart chamber. Then there is the step of identifying mechanical strength of the chamber from the instantaneous volume and pressure.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
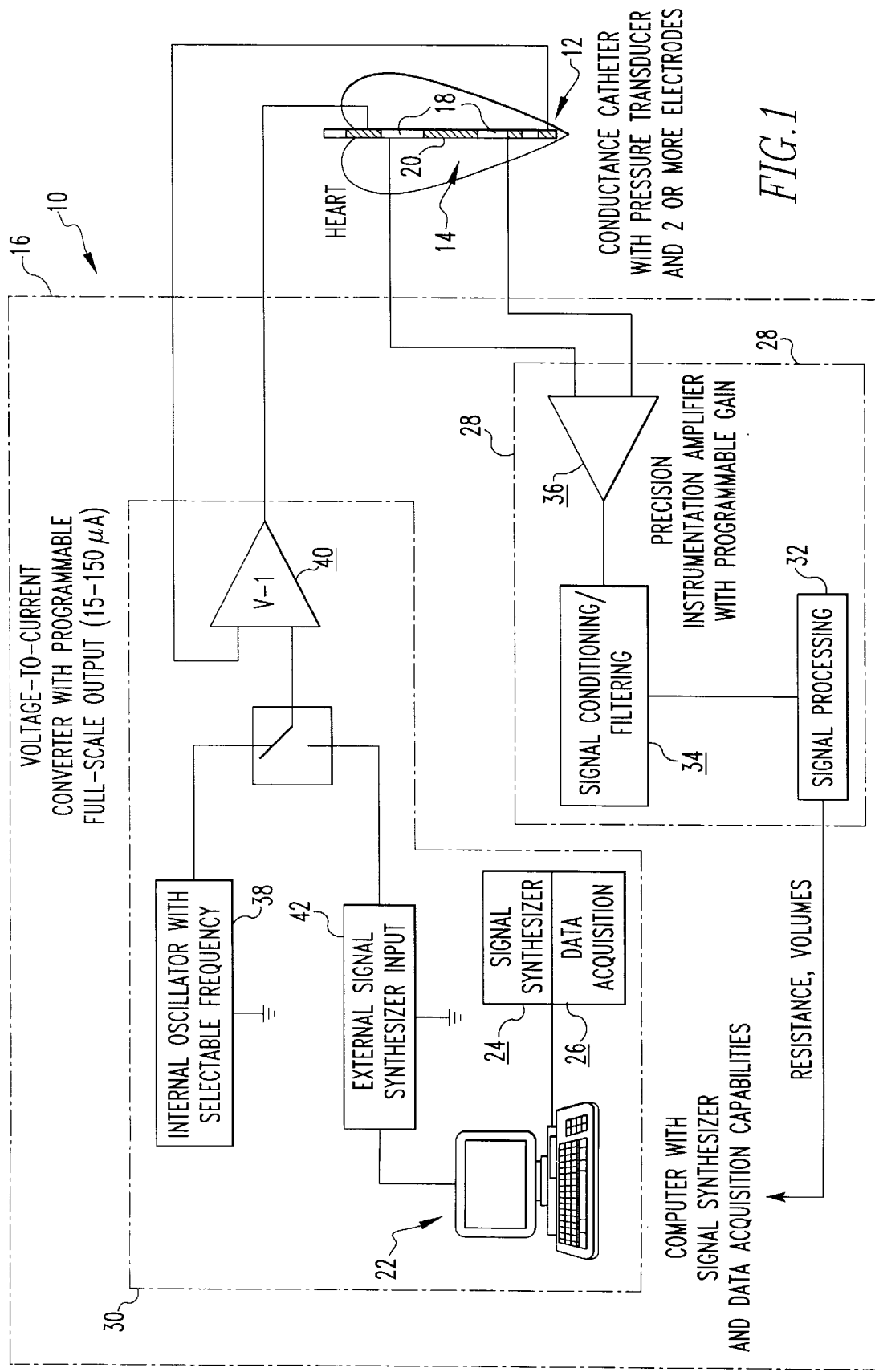
FIG. 1 is a schematic representation of an apparatus of the present invention.

Referring now to the drawings wherein like reference numerals refer to similar or identical parts throughout the several views, and more specifically to FIG. 1 thereof, there is shown an apparatus 10 for determining cardiac performance in a patient. The apparatus 10 comprises a multifrequency conductance catheter 12 for measuring instantaneous volume of a heart chamber. The apparatus 10 comprises a mechanism 14 for measuring instantaneous pressure of the heart chamber. The apparatus 10 comprises a signal processing mechanism 16 for processing the instantaneous volume and the pressure of the heart chamber to identify mechanical strength of the chamber and for automatically producing a plurality of desired waveforms at desired frequencies for the conductance catheter 12. The processing mechanism 16 is connected to the pressure measuring mechanism 14 and the catheter 12.

Preferably, the conductance catheter 12 includes a plurality of electrodes 18 to measure at least one segmental volume of the heart chamber. The conductance catheter 12 preferably includes at least one pressure sensor 20 to measure ventricular pressure in the chamber. Preferably, the electrodes 18 measure the EKG.

The signal processing mechanism 16 preferably combines the instantaneous volume and pressure with a first derivative of pressure to identify the mechanical strength of the chamber.

The signal processing mechanism 16 preferably includes a computer 22 with a signal synthesizer 24 and a data acquisition mechanism 26 connected to the catheter 12. Preferably, the signal processing mechanism 16 includes a mechanism 28 for converting conductance into a volume. The converting mechanism 28 is connected to the catheter 12 and the computer 22. Preferably, the converting mechanism 28 includes signal processing circuitry 32 for converting measured conductance to a volume. The signal processing circuitry 32 is connected to the catheter 12 and the computer 22.

The converting mechanism 28 preferably includes a signal conditioning/filter mechanism 34 for reducing noise level of measured conductance. The signal conditioning/filter mechanism 34 is connected to the signal processing circuitry 32 and the computer 22. Preferably, the converting mechanism 28 includes a precision amplifier 36 which amplifies a potential differential across the electrodes 18, said pressure amplifier 36 connected to the catheter 12 and the signal conditioning/filter mechanism 34.

The signal processing mechanism 16 preferably includes a mechanism 30 for producing a drive signal to drive the conductance catheter 12. The producing mechanism is connected to the catheter 12 and the computer 22.

The drive mechanism 30 preferably includes an internal oscillator 38 which generates an amplitude excitation voltage at least at two different frequencies. The internal oscillator 38 is connected to the computer 22 and the catheter 12. Preferably, the drive mechanism 30 includes a voltage-to-current converter 40 which converts excitation voltage to a current. The voltage-to-current converter 40 is connected to the internal oscillator 38 and the catheter 12. Preferably, the drive mechanism 30 includes a signal synthesizer 24 of the computer 22 which controls the external input signal synthesizer 42, which controls the voltage-to-current converter 40.

The present invention pertains to a method for determining cardiac performance in a patient. The method comprises the steps of applying automatically multifrequencies to a conductance catheter 12.

Then there is the step of measuring the instantaneous volume of a heart chamber of the patient. Next there is the step of measuring the instantaneous pressure of the heart chamber. Then there is the step of identifying mechanical strength of the chamber from the instantaneous volume and pressure. Preferably, the measuring the volume step includes the step of measuring the volume with a conductance catheter 12.

In the operation of the preferred embodiment, the purpose of the multifrequency conductance apparatus 10 is to evaluate ventricular mechanics by means of the pressure-volume relationship. A major component of the apparatus 10 is a device which can measure instantaneous volume from a heart chamber using the conductance catheter 12. The instantaneous volume signal can then be coupled with pressure, and the first derivative of pressure to provide gold standard measures of the mechanical strength of the ventricle. These measures are made by manipulating the preload to the ventricular chamber as instantaneous pressure and volume are plotted against one-another.

The conductance apparatus 10 which can be excited with multiple frequencies is capable of correcting for errors resulting from frequency dependent conductance of surrounding structures, in short, correcting for the effect of parallel conductance. This may allow a change in conductance catheter 12 design where the more proximal driving electrode is moved away from the ventricle, which may improve the homogeneity of electric field within the ventricular chamber. Without proper correction, such an advantage in field distribution is negated by more parallel conductance. The multifrequency conductance apparatus 10 makes such important advances in conductance catheter 12 design feasible.

The apparatus 10 uses a digitally controlled signal synthesizer 24 to drive the conductance catheter 12. This results in consistent and more accurately controlled waveform shape, amplitude and frequency. The use of a digital synthesizer also allows the user to select any type of waveform over a broad range of frequencies to apply to the conductance catheter 12. These two features are unique to this apparatus 10 and not available in the Leycom Sigma 5, or products of other companies including BioMetrics, Inc., Las Vegas, Nev.

The multifrequency conductance apparatus 10 allows the user to set the operating current of the apparatus 10, within a physiologically safe range. The ability of the apparatus 10 to operate at currents higher than the 30 $\mu$A RMS current available with the Leycom Sigma 5 improves the signal to noise ratio of the measured signal. This feature makes the proposed apparatus 10 useful in situations in which the signal to noise ratio may be poor. For example, this apparatus 10 may be used for conductance studies in mouse hearts which have undergone gene manipulation ("knock-out" mice). Pressure-volume relationships are critical in quantitating the physiologic effect of genetic manipulation of a mouse heart. However, the dimensions of the mouse heart require small electrode spacing, producing a poor signal to noise ratio of the measured volume signal. The ability to increase the applied current improves the signal to noise ratio and improves the quality of the measured volume signal in mice. These same results and applications can be used in other animals and in humans. The only change is that an appropriate sized catheter 12 be used for the given patient.

The apparatus 10 consists of multiple components with features outlined in FIG. 1.

(a) The apparatus 10 includes a voltage-controlled constant current source for any configuration of conductance catheter 12 with a means for applying a constant alternating current (AC) using a digital signal synthesizer 24. The digital signal synthesizer 24 is used to select any type of waveform over a broad range of frequencies.

Figure 2:
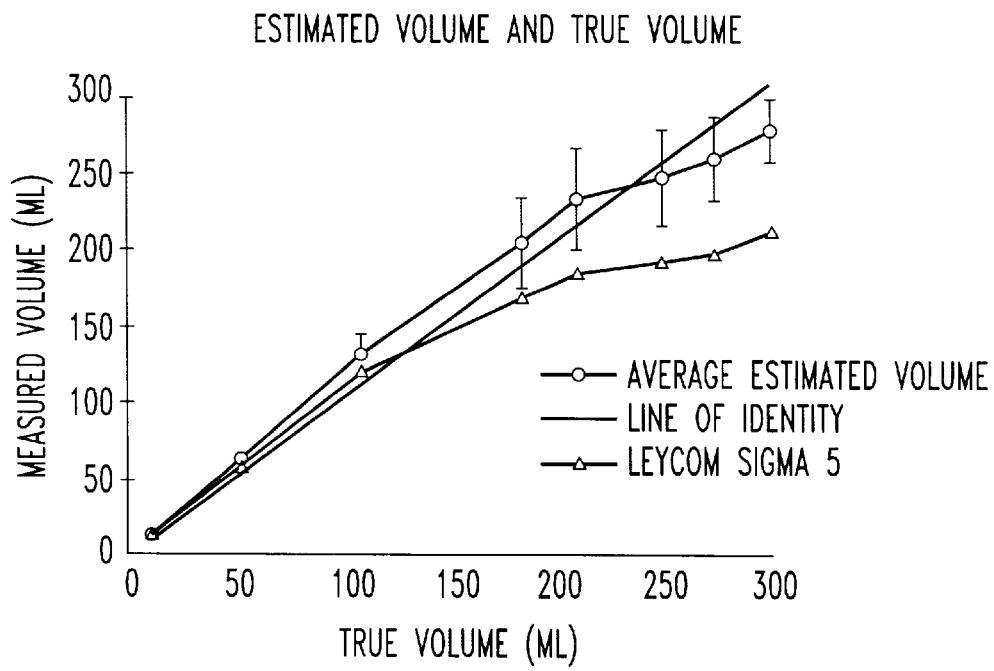
FIG. 2 is a graph of the true volume vs. measured volume.

(b) The apparatus 10 contains analog circuitry which is used for signal conditioning and can be used to measure the conductance signal from any configuration of conductance catheter 12. The conductance signal is converted to volume based on the equation:

$$V = \frac{L^2 * G}{\delta}$$

where V=volume of the heart muscle chamber, L=the distance between the measuring electrodes 18 on the conductance catheter 12, δ=the conductivity of blood, and G=conductance. Data from the apparatus 10 is shown in FIG. 2. The apparatus 10 being disclosed shows improved performance over the existing Leycom Sigma 5.

In FIG. 2, true volume is displayed on the x-axis. Measured conductance volumes for the multifrequency conductance apparatus 10 being disclosed (open circles) are displayed as Mean ±SE for three runs. The measured conductance volumes for the competing Leycom Sigma 5 are also shown (open triangles). The solid line is the line of identity. In larger volumes seen clinically, the device being disclosed estimates true volume more closely than the Leycom Sigma 5 did.

Figure 3:
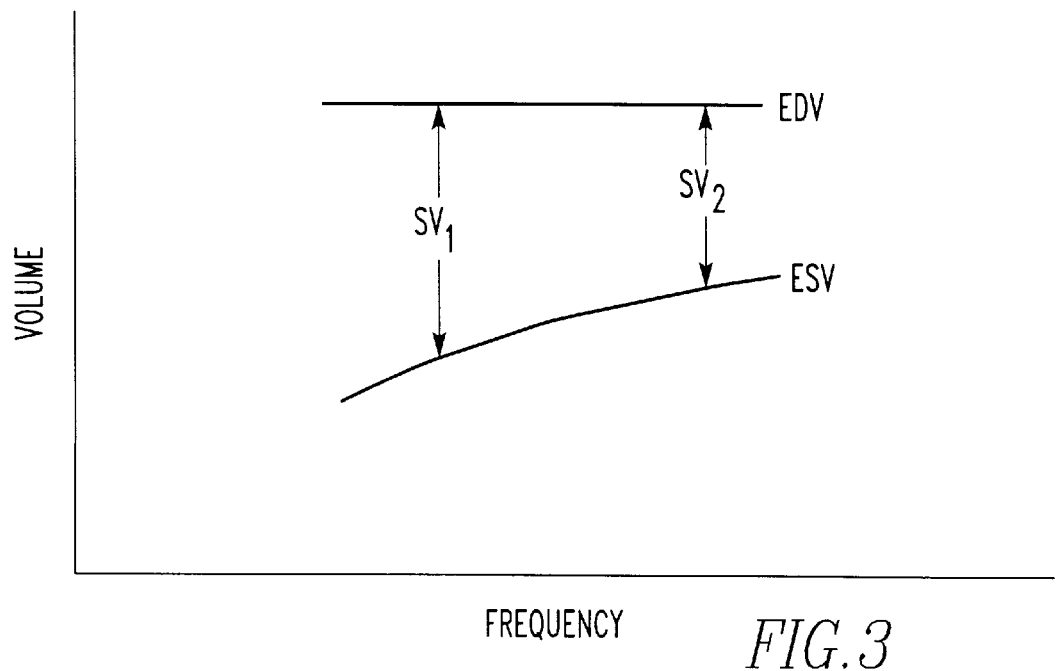
FIG. 3 is a graph of volume vs. frequency.

(c) The apparatus 10 provides a method for estimating the true stroke volume by measuring volume at multiple frequencies. End-contractions (end-systolic) and end-relaxation (end-diastolic) volumes are plotted versus frequency to obtain a linear relationship as illustrated in FIG. 3. The difference between these volumes or the amount of blood ejected by the heart to the body is termed stroke volume (SV). The end-systolic and end-diastolic volumes generated by the multifrequency conductance apparatus 10 and the Leycom Sigma 5 are both artificially large due to parallel conductance. Since SV varies with frequency (i.e. $SV_1 > SV_2$), and ESV and EDV also vary with frequency, parallel conductance can be derived, and true stroke volume, EDV and ESV derived. Once an estimate of the true stroke volume, EDV, and ESV is obtained, all gold standard hemodynamic parameters in conjunction with occlusion of the inferior vena cava can be accurately derived. End-systolic elastance of one patient can be compared to another, which has not been previously possible.

The Leycom Sigma 5 and BioMetrics cannot be used this way because they operate at a single fixed frequency. Since occlusion of the inferior vena cava to change blood pressure on a beat-by-beat basis is used to generate measures of heart muscle strength, current leakage into surrounding heart structures will be changing on a beat-by-beat basis, thus affecting the accuracy in measuring stroke volume, EDV and ESV. As a result, a feature made possible by the apparatus 10 is critical to be able to compare the results of one patient to the next.

(d) The apparatus 10 provides the means for not only acquiring volume but also other signals critical for calculating hemodynamic indices such as pressures in the heart, and the electrocardiogram. All these signals may be acquired and processed using an integrated signal processor.

(e) The apparatus 10 has the software capabilities to calculate gold standard hemodynamic indices to distinguish the strength of the heart (end-systolic pressure volume relationships, preload recruitable stroke work, end-diastolic volume—dP/dt relationship) from the load the heart works against (end-systolic pressure and volume, end-diastolic pressure and volume, effective arterial elastance). Additional indices calculated include stroke volume, stroke work, positive and negative dP/dt, cardiac output, ejection fraction, peak filling rate, peak ejection rate, isovolumic relaxation time constant and preload adjusted maximal power.

The pressure/conductance catheter 12 for mice, model SPR-716, consists of a pressure sensor 20 located near the tip of a 0.25 mm diameter polyimide catheter 12, with two platinum ring electrodes 18 distal to the sensor and two platinum electrodes 18 proximal. The outer two electrodes 18 are spaced 5.5 mm apart, center to center, and the inner pair 4.5 mm apart. This configuration allows for the placement of the catheter 12 within the heart of a 20 gram mouse, with the pressure sensor 20 in the center of the ventricle, the field generating electrodes 18 at opposite ends of the ventricular chamber, one at the apex and one at the aortic valve, and the segment sensing electrodes 18 almost at the same location, but slightly closer to each other, to measure the electrical field distribution within the chamber.

The pressure sensor 20, with a diameter of 0.5 mm, has two strain gauges mounted on a thin flexible diaphragm, insulated and isolated from external fluids by a thin silicone rubber coating. As the diaphragm deflects slightly under applied pressure, the strain gauges change resistance linearly with applied pressure, the one gauge increasing in resistance and the other gauge decreasing. Three wires from the strain gauges, along with a reference air vent to atmosphere, are carried through the catheter 12 to the connector at the proximal end. Within the connector is a resistance network to complete a bridge circuit for the transducer and provide the appropriate standardization of output, temperature compensation and bridge balancing.

The platinum ring electrodes 18 are approximately 0.37 mm in diameter and 0.25 mm long. Each one has a wire attached leading to a separate electrical connector for the conductance control unit. In a typical operating configuration, a 30 μA signal can be applied to the outer pair of field excitation electrodes 18, with the inner pair of electrodes 18 connected to an amplifier for measuring the conductance of the ventricle within the beating heart. Changes in conductance are proportional to the volume of electrically conductive blood within the chamber; the conductance control unit is configured to give an on-line analog signal output proportional to the volume of blood in the beating ventricle.

Computer 22 with Signal Synthesizer and data acquisition capabilities—The conductance-volume measurement apparatus 10 utilize a voltage-to-current converter 40 to generate the excitation field. A computer-controlled external synthesizer provides the user full control on waveform and current amplitude, thus allowing different excitation schemes to be tested to improve measurement accuracy. The data acquisition apparatus 10 allows the user to digitize the resistance or volume signals for post processing and data analysis.

Internal Oscillator 38—generate a fixed amplitude excitation voltage at multiple frequencies.

Voltage-to-current converter 40—convert the excitation voltage to a calibrated constant current over wide range of load.

Conductance catheter 12—contains 2 or more electrodes 18, intracardiac electric field is set up by applying the constant current with the catheter 12, the same or additional electrodes 18 are used to measure conductance in the ventricular chamber from which volumes are calculated.

Presssure amplifier 36—amplify the signal from the solid state pressure sensor 20.

Signal conditioning/filtering—after amplification, the measured signal may be filtered using one of the pre-programmed settings to reduce the noise level.

Signal processing circuitry 32—the measured conductance are converted to volume using processing techniques such as envelope detector and synchronous detector. The unprocessed signals is also available to the user for advanced signal analysis.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for determining cardiac performance in a patient comprising:
   a multifrequency conductance catheter for measuring instantaneous volume of a heart chamber;
   a mechanism for measuring instantaneous pressure of the heart chamber; and
   a mechanism for signal processing the instantaneous volume and the pressure of the heart chamber to identify mechanical strength of the chamber and for automatically producing a plurality of desired waveforms at desired frequencies for the conductance catheter, said processing mechanism connected to the pressure measuring mechanism and the volume measuring mechanism.

2. An apparatus as described in claim 1 wherein the signal processing mechanism combines the instantaneous volume and pressure with a first derivative of pressure to identify the mechanical strength of the chamber.

3. An apparatus as described in claim 2 wherein the conductance catheter includes a plurality of electrodes to measure at least one segmental volume of the heart chamber.

4. An apparatus as described in claim 3 wherein the conductance catheter includes at least one pressure sensor to measure ventricular pressure in the chamber.

5. An apparatus as described in claim 4 wherein the electrodes measure the EKG.

6. An apparatus as described in claim 5 wherein the signal processing mechanism includes a computer with a signal synthesizer and a data acquisition mechanism connected to the catheter.

7. An apparatus as described in claim 6 wherein the signal processing mechanism includes a mechanism for converting conductance into a volume, said converting mechanism connected to the catheter and the computer.

8. An apparatus as described in claim 7 wherein the signal processing mechanism includes a mechanism for producing a drive signal to drive the conductance catheter, said producing mechanism connected to the catheter and the computer.

9. An apparatus as described in claim 8 wherein the converting mechanism includes signal processing circuitry for converting measured conductance to a volume, said signal processing circuitry connected to the catheter and the computer.

10. An apparatus as described in claim 9 wherein the converting mechanism includes a signal conditioning/filter mechanism for reducing noise level of measured conductance, said signal conditioning/filter mechanism connected to the signal processing circuitry and the computer.

11. An apparatus as described in claim 10 wherein the converting mechanism includes a pressure amplifier which amplifies the signal from the solid state pressure sensor, said pressure amplifier connected to the catheter and the signal conditioning/filter mechanism.

12. An apparatus as described in claim 11 wherein the drive mechanism includes an internal oscillator which generates an amplitude excitation voltage at least at two different frequencies, said internal oscillator connected to the computer and the catheter.

13. An apparatus as described in claim 12 wherein the drive mechanism includes a voltage-to-current converter which converts excitation voltage to a current, said voltage-to-current converter connected to the internal oscillator and the catheter.

14. An apparatus as described in claim 13 wherein the drive mechanism includes an external input signal synthesizer mechanism for controlling the signal synthesizer of the computer to produce desired waveforms at desired frequencies, said external input signal synthesizer mechanism connected to the computer.

15. A method for determining cardiac performance in a patient comprising the steps of:
   applying automatically multifrequencies to a conductance catheter;
   measuring the instantaneous volume of a heart chamber of the patient;
   measuring the instantaneous pressure of the heart chamber; and
   identifying mechanical strength of the chamber from the instantaneous volume and pressure.

16. A method as described in claim 15 wherein the measuring the first volume step includes the step of measuring the volume with a conductance catheter.

* * * * *